US007820719B2

United States Patent
Schmidt

(10) Patent No.: US 7,820,719 B2
(45) Date of Patent: Oct. 26, 2010

(54) CYTOSTATIC DRUG COMPOSITION

(75) Inventor: Oskar Schmidt, Vienna (AT)

(73) Assignee: Geopharma Produktions GmbH, Vienna (AT)

( * ) Notice: Subject to any disclaimer, the term of this patent is extended or adjusted under 35 U.S.C. 154(b) by 0 days.

(21) Appl. No.: 11/197,465

(22) Filed: Aug. 3, 2005

(65) Prior Publication Data

US 2006/0034795 A1  Feb. 16, 2006

Related U.S. Application Data

(63) Continuation of application No. PCT/AT2004/000023, filed on Jan. 22, 2004.

(30) Foreign Application Priority Data

Feb. 4, 2003  (AT) ................ A 174/2003

(51) Int. Cl.
 *A01N 37/52* (2006.01)
 *A61K 31/155* (2006.01)
(52) U.S. Cl. ..................................... 514/634
(58) Field of Classification Search ............... 514/634
 See application file for complete search history.

(56) References Cited

U.S. PATENT DOCUMENTS 2,336,605 A    12/1943    Ernsberger et al.

FOREIGN PATENT DOCUMENTS

| EP | 1990 0121254 | 8/1991 |
|---|---|---|
| EP | 1990 0121255 | 8/1991 |
| SU | 1816769 | 5/1993 |
| WO | WO 01/85676 | 11/2001 |

OTHER PUBLICATIONS

Gurjal et al., Emerging Drugs (2000), 5(3):273-285.*
Astra Zeneca (2004) 1 page.*
www.tribunes.com-the cancer Journal vol. 8 (3) 1995 1-4.*
Barry J1404 Apr. 2002 1 pg Prevention of Crown Galls (plant cancer) in plant) is of interest.*

* cited by examiner

*Primary Examiner*—Michael G Hartley
*Assistant Examiner*—Shirley V Gembeh
(74) *Attorney, Agent, or Firm*—Baker Botts L.L.P.

(57) ABSTRACT

A drug composition containing as a drug substance a polymeric guanidine derivative based on a diamine containing oxyalkylene chains between two amino groups, with the guanidine derivative representing a product of polycondensation between a guanidine acid addition salt and a diamine containing polyalkylene chains between two amino groups, as well as the pharmaceutically acceptable salts thereof.

4 Claims, No Drawings

CYTOSTATIC DRUG COMPOSITION

CROSS REFERENCE TO RELATED APPLICATIONS

This application is a continuation of International Patent Application No. PCT/AT2004/000023 filed Jan. 22, 2004, designating the United States and published in German on Aug. 19, 2004 under International Patent Publication No. WO 2004/069898, which is based on Austrian Patent Application No. A 174/2003 filed Feb. 4, 2003, to each of which priority is claimed, and each of which is incorporated by reference in its entirety herein.

FEDERALLY FUNDED GRANT SUPPORT

Not applicable.

INTRODUCTION

The invention relates to a drug composition, in particular a cytostatic drug.

BACKGROUND OF THE INVENTION

In the Western civilization, a third of the population suffers from cancer with a mortality rate of no less than 75%. Malignant tumors are nowadays treated cytostatically.

The main problem with the chemotherapy of those diseases is that the cancer cells respond to the applied cytostatic drug only to a certain percentage. Moreover, a complete remission often cannot even be expected if the tumor does respond to the treatment.

A current trend toward an efficiency increase of the chemotherapy consists in the polychemotherapy, i.e. the use of several cytostatic drugs. More and more frequently, various cytostatic drugs with different application points are combined in order to improve the cancer therapy. Thereby, better efficacy is achieved on the one hand and on the other hand the problem of a progressively developing resistance is countered.

A further possibility consists in selectively protecting the healthy cells from the cytostatic drug by a simultaneous administration of cytoprotectors, whereby a higher dose can be administered, at the same time involving fewer side effects (e.g. taxanes).

Despite those measures, the side-effect rate of chemotherapy is still very high. Precisely for this reason it is of utmost importance to develop drug substances which exhibit good efficacy as well as good tolerance, i.e. which possess a therapeutic window that is as broad as possible.

SUMMARY OF THE INVENTION

The invention aims at providing a cytostatic drug which, in comparison with conventional cytostatic drugs such as 5-fluorouracil, cisplatin, epirubicin and mitomycin C, has a broader therapeutic window. The drug composition according to the invention contains as a drug substance a polymeric guanidine derivative.

DETAILED DESCRIPTION OF THE INVENTION

The drug composition according to the invention contains as a drug substance a polymeric guanidine derivative based on a diamine containing oxyalkylene chains between two amino groups, with the guanidine derivative representing a product of polycondensation between a guanidine acid addition salt and a diamine containing polyalkylene chains between two amino groups, as well as the pharmaceutically acceptable salts thereof.

A preferred embodiment of the drug composition according to the invention is characterized in that, among the representatives of the family of polyoxyalkylene guanidine salts, there are such using triethylene glycol diamine (relative molecular mass: 148), polyoxypropylene diamine (relative molecular mass: 230) as well as polyoxyethylene diamine (relative molecular mass: 600).

Most preferably poly-[2-(2-ethoxyethoxyethyl)guanidinium hydrochloride] comprising at least 3 guanidinium groups is contained as the drug substance, with the average molecular mass in particular ranging from 500 to 3,000 D.

Furthermore, the invention relates to the use of a polymeric guanidine derivative based on a diamine containing oxyalkylene chains between two amino groups, with the guanidine derivative representing a product of polycondensation between a guanidine acid addition salt and a diamine containing polyalkylene chains between two amino groups, as well as the pharmaceutically acceptable salts thereof, for the preparation of a cytostatically active drug composition.

Furthermore, the invention relates to the use of polyoxyalkylene guanidine salts produced by using triethylene glycol diamine (relative molecular mass: 148), polyoxypropylene diamine (relative molecular mass: 230) as well as polyoxyethylene diamine (relative molecular mass: 600).

The polymeric guanidine derivatives used in accordance with the invention are known from PCT/AT01/00134. By way of reference, the content of said literature is incorporated in the present specification.

WORKING EXAMPLES

The preparation of a preferred representative of the compounds used in accordance with the invention as well as the detection of the cytostatic activity are described in the following.

Substitutionally for the class of compounds used in accordance with the invention, the cytostatic activity of poly-[2-(2-ethoxyethoxyethyl)guanidinium hydrochloride] with an average molecular mass of 1000 D is described hereafter (CAS No. 374572-91-5).

In order to prepare said compound, 4.43 moles of guanidinium hydrochloride were dissolved in 4.03 moles of triethylene glycol diamine at 50° C. Subsequently, this was heated to 120° C. and stirred for 2 hours at said temperature. Thereafter, said temperature was maintained for 2 hours, then a vacuum (0.1 bar) was applied and stirring under vacuum was continued for 2 more hours at 170° C. Subsequently, this was aerated at normal pressure, cooled to 120° C. and diluted with demineralized water to approximately 50%. It was neutralized to a pH of approximately 6 with phosphoric acid, allowed to cool and diluted to the desired concentration. The molecular weight was determined to be 1000 D.

Establishing the Cytostatic Activity:

Cell lines of a colon carcinoma and a pancreas carcinoma, such as Capan-1, DLD-1, HT 29, HCT-8, MLA-PA-CA2, PANCI, BXPC-3, ASPC-1, and HT-29, were examined. The tested cancer cell lines were stored in liquid nitrogen. After defrosting, the cancer cells were cultivated in culture flasks with RPMI-1640+glutamine medium (Gibco® No. 5240025) at 37° C./5% $CO_2$ atmosphere for up to 14 days so that a monolayer of cells was able to form. Thereupon, the cells were harvested with trypsin+EDTA (Gibco® No. 15400-054) and washed twice with an RPMI-medium.

In addition, lymphocytes of healthy test persons were examined. In doing so, a total amount of 100 ml blood was drawn into EDTA test tubes. The lymphocytes were isolated from the full blood by means of a Mono-Poly Resolving Medium/Ficol-Hypaque gradient, were washed three times with an HBSS buffer and, prepared in this manner, they were added to the test stock.

Apart from poly-[2-(2-ethoxyethoxyethyl)guanidinium hydrochloride], the chemotherapeutic agents cisplatin, epirubicin, mitomycin C and 5-fluorouracil were tested by way of comparison. Therefor, the compounds were at first dissolved according to the respective instructions of the manufacturer and were then stored as a stock solution in aliquots of 1 ml each (concentration of drug substance: 1000 µg/ml) in liquid nitrogen at −180° C. The dissolved substances were used on the very same day.

In order to determine the cytotoxic activity of the substances, the cancer cells were transferred from the culture flasks with an RPMI-washed suspension at a concentration of 20,000 cells in 200 µl onto microtiter plates. In the presence of varying concentrations of the test substances, the cancer cells were subsequently incubated for three days at a temperature of 37° C. and in an atmosphere of 5% $CO_2$. For the poly-[2-(2-ethoxyethoxyethyl)guanidinium hydrochloride], concentrations of 0.12 to 500 µg/ml (factor 2 dilutions) were used in all test arrangements. After three days of incubation, the evaluation was carried out by means of the nonradioactive cell proliferation and cytotoxicity test EZ4U (Biomedica No. BI-5000 10×96 determinations). After three hours of incubation with EZ4U, the evaluation was carried out photometrically in percent at a wavelength of 49/630 nm in a slidephotometer (extinction of the test sample divided by extinction of the control-sample blank value).

The vitality of the lymphocytes was determined in a suspension of $1.2 \times 10^7$/ml at varying concentrations of the test substances. In the presence of the test substances, the cell suspensions were incubated for 24 hours at 37° C. and in an atmosphere of 5% $CO_2$ and were then dyed with trypan blue. After dyeing, the lymphocytes were applied onto the counting chamber and their vitality was evaluated in percent.

The drug substance poly-[2-(2-ethoxyethoxyethyl)guanidinium hydrochloride] exhibits favorable pharmacodynamic properties, along with low toxicity and good tolerance from a pharmacological point of view, and can therefore be used as a medicine in oncological therapy. The substance shows in particular an excellent cytostatic activity, as can be demonstrated by tests using several cancer cell lines, e.g. of a colon carcinoma (HT-29, HCT-8, DLD-1) or a pancreas carcinoma (ASPC-1, BXPC-3, CAPAN-1, PANC-1).

In addition, the drug substance used in accordance with the invention possesses a broad therapeutic window since in healthy endogenous cells such as lymphocytes the cytostatic activity has been observed only at concentrations starting from 100 µg/ml (table 4) while in cancer cells said activity occurs already at concentrations starting from 2 to 16 µg/ml (tables 1 and 2). By way of comparison, table 3 shows the cytostatic activity of 5-fluorouracil, cisplatin, epirubicin and mitomycin C.

After an (intravenous or intraperitoneal) systemic administration of poly-[2-(2-ethoxyethoxyethyl)guanidinium hydrochloride] in amounts of up to 15 mg/kg body weight, serum concentrations of up to 100 µg/ml are measured in the rat's blood after two hours, whereby, at the same time, the tolerance is good. Therefore, poly-[2-(2-ethoxyethoxyethyl) guanidinium hydrochloride] can be used as a cytostatic drug.

The drug substances used in accordance with the invention can be processed to pharmaceutical preparations in a manner known per se, either alone or together with inorganic or organic pharmacologically indifferent adjuvants.

TABLE 1

Cytostatic activity in comparison with different cell lines of a colon carcinoma (vitality in %)

| Test compound* Concentration (µg/ml) | HAT-29 | HCT-8 | DLD-1 | HCT-15 | Colon 320DM | Colon 205 |
|---|---|---|---|---|---|---|
| 64 | 11 | 11 | 15 | 16 | 21 | 15 |
| 32 | 13 | 15 | 17 | 18 | 22 | 16 |
| 16 | 21 | 34 | 26 | 25 | 24 | 16 |
| 8 | 47 | 91 | 49 | 69 | 26 | 27 |
| 4 | 76 | 114 | 86 | 81 | 37 | 59 |
| 2 | 77 | 90 | 103 | 81 | 79 | 70 |
| 1 | 88 | 85 | — | — | — | — |
| 0.5 | 98 | 79 | — | — | — | — |
| 0.25 | 85 | 70 | — | — | — | — |
| 0.125 | 76 | 88 | — | — | — | — |

*Poly-[2-(2-ethoxyethoxyethyl)guanidinium hydrochloride]

TABLE 2

Cytostatic activity in comparison with different cell lines of a pancreas carcinoma (vitality in %)

| Test compound* Concentration (µg/ml) | AsPc-1 | BxPc-3 | Capan-1 | Panc-1 | MIA PaCa-2 |
|---|---|---|---|---|---|
| 64 | 13 | 9 | 46 | 11 | 11 |
| 32 | 12 | 11 | 79 | 16 | 12 |
| 16 | 15 | 18 | 114 | 30 | 16 |
| 8 | 50 | 44 | 95 | 55 | 58 |
| 4 | 70 | 74 | 111 | 90 | 97 |
| 2 | 92 | 63 | 115 | 88 | 106 |

*Poly-[2-(2-ethoxyethoxyethyl)guanidinium hydrochloride]

TABLE 3

Cytostatic activity of standard chemotherapeutic agents in comparison with different cell lines of pancreas carcinoma (vitality in %)

| Substance | concentration in µg/ml | AxPc-1 | BxPc-3 | Capan-1 | Panc-1 |
|---|---|---|---|---|---|
| 5-Fluorouracil | 60 | 71 | 67 | 23 | 62 |
| | 6 | 88 | 79 | 38 | 77 |
| | 0.6 | 92 | 86 | 46 | 80 |
| Cisplatin | 2.5 | 53 | 93 | 36 | — |
| | 0.25 | 89 | 65 | 54 | — |
| | 0.025 | 85 | 87 | 94 | — |
| Epirubicin | 11.9 | 55 | 62 | 54 | 61 |
| | 1.19 | 59 | 55 | 35 | 43 |
| | 0.12 | 105 | 76 | 50 | 111 |
| Mitomycin C | 1.5 | 65 | 47 | 22 | 55 |
| | 0.15 | 89 | 91 | 30 | 103 |
| | 0.015 | 98 | 100 | 59 | 104 |

TABLE 4

Vitality of lymphocytes in %

| Test compound* Concentration (µg/ml) | |
|---|---|
| 1000 | 1 |
| 500 | 16 |
| 250 | 30 |

TABLE 4-continued

| Vitality of lymphocytes in % | |
|---|---|
| Test compound* Concentration (μg/ml) | |
| 100 | 98 |
| 50 | 96 |
| 25 | 100 |
| 12.5 | 98 |

*Poly-[2-(2-ethoxyethoxyethyl)guanidinium hydrochloride]

I claim:

1. A method of producing a cytostatic effect on a pancreatic cancer cell comprising exposing the pancreatic cancer cell to a concentration of less than 100 μg/ml of a drug substance selected from the group consisting of a product of polycondensation between a guanidine acid addition salt and a diamine compound comprising an oxyalkylene chain between two amino groups, and a pharmaceutically acceptable salt thereof, where said amount is selectively cytostatic to the pancreatic cancer cell, and wherein the diamine is selected from the group consisting of triethylene glycol diamine (relative molecular mass: 148), polyoxypropylene diamine (relative molecular mass: 230) and polyoxyethylene diamine (relative molecular mass: 600).

2. The method according to claim 1, wherein the drug substance is poly-[-(2-ethoxy-ethoxyethyl)guanidinium hydrochloride).

3. A method of producing a cytostatic effect on a colon cancer cell comprising exposing the colon cancer cell to a concentration of less than 100 μg/ml of a drug substance selected from the group consisting of a product of polycondensation between a guanidine acid addition salt and a diamine compound comprising an oxyalkylene chain between two amino groups, and a pharmaceutically acceptable salt thereof, where said amount is selectively cytostatic to the colon cancer cell, and wherein the diamine is selected from the group consisting of triethylene glycol diamine (relative molecular mass: 148), polyoxypropylene diamine (relative molecular mass: 230) and polyoxyethylene diamine (relative molecular mass: 600).

4. The method according to claim 3, wherein the drug substance is poly-[2-(2-ethoxy-ethoxyethyl)guanidinium hydrochloride).

* * * * *